(12) United States Patent
Gauckler et al.

(10) Patent No.: US 10,265,672 B2
(45) Date of Patent: Apr. 23, 2019

(54) MICROCAPSULE

(71) Applicant: Holcim Technology Ltd., Jona (CH)

(72) Inventors: Ludwig Julius Gauckler, Schaffhausen (CH); Urs Thomas Gonzenbach, Zürich (CH); Philip Noah Sturzenegger, Zürich (CH); Franziska Krauss Juillerat, Praden (CH)

(73) Assignee: Holcim Technology Ltd., Rapperswil-Jona (CH)

( * ) Notice: Subject to any disclaimer, the term of this patent is extended or adjusted under 35 U.S.C. 154(b) by 0 days.

(21) Appl. No.: 15/804,750

(22) Filed: Nov. 6, 2017

(65) Prior Publication Data
US 2018/0085724 A1 Mar. 29, 2018

Related U.S. Application Data

(62) Division of application No. 13/991,417, filed as application No. PCT/IB2011/002480 on Oct. 17, 2011, now Pat. No. 9,827,545.

(30) Foreign Application Priority Data

Dec. 3, 2010 (EP) .................... 10015281

(51) Int. Cl.
| | | |
|---|---|---|
| *A23L 27/00* | (2016.01) | |
| *B01J 13/02* | (2006.01) | |
| *B01J 13/20* | (2006.01) | |
| *A61K 9/50* | (2006.01) | |
| *F28D 20/02* | (2006.01) | |

(52) U.S. Cl.
CPC .............. *B01J 13/025* (2013.01); *A23L 27/72* (2016.08); *B01J 13/02* (2013.01); *B01J 13/20* (2013.01); *A61K 9/501* (2013.01); *F28D 20/023* (2013.01); *Y10T 428/2982* (2015.01); *Y10T 428/2984* (2015.01); *Y10T 428/2989* (2015.01)

(58) Field of Classification Search
CPC ......... A23L 27/72; B01J 13/02; B01J 13/025; B01J 13/20; A61K 9/501; F28D 20/023; Y10T 428/2982; Y10T 428/2984; Y10T 428/2989
See application file for complete search history.

(56) References Cited

U.S. PATENT DOCUMENTS

| | | | |
|---|---|---|---|
| 6,210,715 B1 | 4/2001 | Starling et al. | |
| 2002/0155144 A1 | 10/2002 | Troczynski et al. | |
| 2009/0325780 A1 | 12/2009 | Gauckler et al. | |
| 2010/0144562 A1 | 6/2010 | Quercia et al. | |

FOREIGN PATENT DOCUMENTS

| | | | |
|---|---|---|---|
| DE | 10 2007 023491 A1 | | 11/2008 |
| WO | WO 2007009455 | * | 1/2007 |
| WO | 2007/068127 A1 | | 6/2007 |

OTHER PUBLICATIONS

International Search Report dated Mar. 28, 2012, issued in International Application PCT/IB2011/002480.
Written Opinion of the International Searching Authority (PCT Rule 66), dated Jan. 21, 2013, issued in International Application PCT/IB2011/002480.
Written Opinion of the International Searching Authority (PCT Rule 43bis.1), issued in International Application PCT/IB2011/002480.

* cited by examiner

*Primary Examiner* — Irina S Zemel

(74) *Attorney, Agent, or Firm* — Fitch, Even, Tabin & Flannery LLP

(57) ABSTRACT

A method for the production of a microcapsule, in particular a microcapsule of spherical shape having a hollow capsule space therein, includes the steps of: a) preparing of a suspension of particulate cementitious material in a solvent b) preparing a dispersion by mixing the suspension of step a) with an immiscible fluid so that (i) the suspension is present as a dispersed phase in the fluid as a dispersion medium or that (ii) the fluid is present as the dispersed phase in the suspension as the dispersion medium, such that the particulate material of the suspension adsorbs at least partially at a phase boundary between the fluid and the suspension, and c) allowing the particulate material adsorbed at the phase boundary to hydrate with the formation of a microcapsule.

15 Claims, 4 Drawing Sheets

MICROCAPSULE

CROSS-REFERENCE TO RELATED APPLICATIONS

This Application is a divisional application of U.S. application Ser. No. 13/991,417 filed Jun. 3, 2013, which is the U.S. National Stage Application filed under 35 U.S.C. § 371 of International Application PCT/IB2011/002480, filed Oct. 17, 2011, designating the United States, and claims priority from EP Application 10 015 281.8, filed Dec. 3, 2010, the complete disclosures of which are hereby incorporated herein by reference in their entirety for all purposes.

TECHNICAL FIELD

The invention relates to a microcapsule, in particular of spherical shape, comprising a hollow capsule space encased by a capsule shell. Furthermore, the invention relates a method for the production of a microcapsule.

BACKGROUND ART

Microencapsulation was first introduced by Green and Schleicher in the 1950s to produce pressure-sensitive dye microcapsules for carbonless copying paper. Since the mid-1970s, microencapsulation has become increasingly popular in pharmaceutical and food technology. Nowadays, mechanically stable capsules are used as fillers to reduce weight and impact force of mechanical parts. Buildings are passively conditioned with mortars containing encapsulated phase change materials. Handling pesticides is much safer if the hazardous substances are encapsulated. In nutrition industry, high added value additives like flavors, vitamins or fatty acids are encapsulated and screened from premature degradation. A lot of effort is invested in adopting microencapsulation technology to deliver active agents in medicine where encapsulated drugs should safely be delivered at specific target sites.

An ideal encapsulation system features an efficient loading mechanism and yields in microcapsules with tunable size and size distribution, permeability and release kinetics as well as a high specific cargo volume. Additionally, the system allows adjusting the mechanical properties of the capsules independently from their permeability.

Particle-stabilized microcapsules are a relatively new class of capsules with great potential to meet many of those specifications. Their formation is based on the emulsion templating concept first proposed by Velev et al. in 1996 [Velev, O. D., K. Furusawa, and K. Nagayama, Assembly of latex particles by using emulsion droplets as templates. 1. Microstructured hollow spheres. Langmuir, 1996. 12(10): p. 2374-2384]. Thereby, capsules with defined pore sizes can be synthesized by the self assembly of particles at the interface of emulsion droplets.

Inorganic capsules belong to a special class of microcapsules. WO 2007/068127 A1 (ETH Zurich) discloses e.g. a method for the modification of particle wettability and the formation of particle-stabilized foams. This method can be applied as well for the formation of inorganic microcapsules. Compared to state of the art co-polymer, polyelectrolyte or amphiphile vesicles, inorganic microcapsules generally exhibit higher chemical and thermal resistance as well as improved environmental compatibility. Their release kinetics can be tailored by using coarser or finer particles in order to adapt the pore size within the capsule shell [Dinsmore, A. D., et al., Colloidosomes: Selectively permeable capsules composed of colloidal particles. Science, 2002. 298(5595): p. 1006-1009]. However, the finer the particles are, the weaker the capsule shells generally become.

Unfortunately, the mechanical stability of porous inorganic microcapsule shells is in general rather low what often leads to disintegration or folding of the structures upon drying. Such coupling between system properties is undesirable and leaves room for improvement.

SUMMARY OF THE INVENTION

It is therefore an object of the invention to provide improved microcapsules which in particular feature enhanced mechanical properties and which are suitable for various applications in different fields of technology. A further object of the present invention is to provide a flexible method for the production of microcapsules.

The solution of the invention in view of the microcapsules is specified by the features of claim 1. According to the invention the microcapsule comprises a hollow capsule space encased by a capsule shell and the capsule shell is at least partially made of hydrated cementitious material.

Within the context of the invention, the term "microcapsule" in particular stands for capsules with a maximum length or dimension in the range of 0.01-10,000 µm. In other words, the term microcapsule covers particles from the sub-micron or nanometer range up the millimeter range. The microcapsule can have any shape, in particular spherical, elongated, ellipsoidal, oblate ellipsoidal, cylindrical or even unsteady.

A hollow capsule space is a cavity the size of which is defined by the shell of the microcapsule.

A "hydrated cementitious material" as used herein is in particular a hydrated inorganic material. Especially, the hydrated cementitious material is an inorganic and preferably water insoluble material which has hardened because of a chemical hydration reaction. Especially, the chemical reaction results when anhydrous and unhydrated cementitious material, e.g. in the form of a powder, is brought into contact with water and produces hydrates that are preferably insoluble in water. When producing the hydrates, water is added to the crystal structure of the cementitious material. However, the term "hydration" as used herein should not be mixed up with organic hydration reactions where water molecules are decomposed and added to a molecular structure or the formation of a hydration shell around metals, ions or dipolar molecules dissolved in water.

Compared to known microcapsules, the inventive capsules show a very high mechanical stability which allows the harvesting of intact single dry capsules. In addition, the microcapsules feature a microstructure which is highly suitable for various applications in the fields of e.g. medicine, pharmaceuticals, nutrition, agriculture, constructions or building technology. Owing to their unique microstructure, the inventive microcapsules show very interesting mechanical properties, especially an excellent crack tolerance and elasticity, coupled with good compressive strength. As well, the inventive microcapsules are very stable, even at high temperatures, chemically inert and in general harmless to the environment.

The inventive microcapsules can be produced in very reliable and economic production processes. Thereby, it is possible to fine tune e.g. the mechanical properties, chemical composition, porosity and size of the capsule shell in a broad range by deliberately controlling the production process. In addition, it has been found that the inventive microcapsules comprising hydrated cementitious material are in general highly compatible with numerous fluids, liquids and solids. This makes these capsules interesting for various release applications in different fields of technology.

Preferably, the hydrated cementitious material comprises hydrated portland cement, calcium aluminate cements, calcium sulfoaluminate cement, phosphate cements, hydrated alumina binder, hydrated supplementary cementitious materials (SCM) like slag (a by-product of smelting ore), pozzolan, lime stone etc. or combinations thereof. These materials have proven to be very suitable for the inventive microcapsules.

According to an especially preferred embodiment, the hydrated cementitious material comprises hydrated calcium aluminate cement and/or slag. Microcapsules comprising hydrated calcium aluminate and/or slag can be made with unexpected high crack tolerance and elasticity, coupled with good compressive strength. Furthermore, microcapsules comprising hydrated calcium aluminate and/or slag are highly stable also at high temperatures, chemically inert and harmless to the environment.

In case the hydrated cementitious material comprises hydrated slag, a hydrated ground granulated blast furnace slag (GBFS) is preferred. Ground granulated blast furnace slag is e.g. obtainable by quenching molten iron slag that is a by-product of iron and steel production from a blast furnace in water or steam, to produce a glassy, granular product that is then dried and ground into a fine powder with cementitious properties. If the microcapsule comprises hydrated ground granulated blast furnace slag as hydrated cementitious material the strength and durability of the microcapsule is significantly improved.

However, other cementitious materials may be used for the capsule shell as well and may even be advantageous for specific applications. However, it may be advantageous to avoid the use of fly ash or calcium aluminate, so that the microcapsule is free of fly ash or calcium aluminate.

The hydrated cementitious material may preferably constitute a major component of the capsule shell. It is to be noted that this does not necessarily mean that the weight proportion of the hydrated cementitious material is more than 50% by weight. If the capsule consists of e.g. three (or more) compounds the proportion of the major component may be lower than 50% (e.g. 40%) while each of the other components has a lower proportion than the major component. The hydrated cementitious material is the component with the largest weight proportion of all components of the capsule shell in this case.

Especially preferred, a weight proportion of the hydrated cementitious material is 25% by weight or more, preferably 50% by weight or more, more preferably 75% by weight or more, most preferably 90% by weight or more with respect to the weight of the capsule shell.

In a highly preferred embodiment, the capsule shell consists essentially of hydrated cementitious material only. In other words, apart from unavoidable impurities the capsule shell consists only of hydrated cementitious material in this case.

If the hydrated cementitious material constitutes a major component of the capsule shell, the stability and mechanical properties can significantly be improved. As it has surprisingly been proven, the higher the weight proportion of the hydrated cementitious material, the better the overall crack tolerance, elasticity and compressive strength of the microcapsule. This is especially true for weight proportions of more than 90% by weight or if the capsule shell consists essentially of hydrated cementitious material only.

But it is also possible to provide a capsule shell where the hydrated cementitious material does not constitute a major component. This may e.g. be advantageous for specific applications of the microcapsules.

Preferably, the shell comprises additional material, in particular a non-hydraulic material. The non-hydraulic material is preferably a metallic, polymeric and/or ceramic material. Put differently, the shell preferably features a composite structure with non-hydraulic material. Thereby, the mechanical and chemical properties of the capsule shell can be further tailored in view of specific applications.

Especially preferable, the shell comprises a layered structure, preferably with at least two layers having different chemical compositions and/or comprising different materials.

In a first preferred embodiment with a layered shell structure, an innermost layer comprises at least a portion of the hydrated cementitious material, whereas an outermost layer comprises at least a portion of the non-hydraulic material.

Even more preferred, the innermost layer comprises all of the hydrated cementitious material whereas the outermost layer is essentially free of hydrated cementitious material. Microcapsules with such kind of layered shell structures are highly beneficial because the outer side of the microcapsule can be adapted even to delicate environmental conditions (e.g. in physiological fluids) while at the same time advantageous mechanical properties can be preserved.

In a second preferred embodiment with a layered shell structure, an innermost layer comprises at least a portion of the non-hydraulic material, whereas an outermost layer comprises at least a portion of the hydrated cementitious material. More preferably in this case, the outermost layer comprises all of the hydrated cementitious material whereas the innermost layer is essentially free of hydrated cementitious material. Such shell structures are especially beneficial if the microcapsule is used as load-carrying member for delicate liquids and solids in release applications. Thereby, the compatibility of the microcapsule with various fluids and solids can further be enhanced.

An outer diameter of the microcapsule is preferably in the range of 0.5-500 µm (micron), more preferably 1-200 µm (micron) and even more preferably 5-100 µm (micron). The thickness of the hydrated cementitious shell is 0.1-10 µm, more preferred 0.2-5 µm, most preferred 0.5-2 µm. In the case of non spherical microcapsules, the term "diameter" stands in particular for a maximum outer dimension of the microcapsule. Microcapsules comprising hydrated cementitious material and an outer diameter in the range of 0.5-500 µm show excellent mechanical properties, especially concerning crack tolerance and elasticity as well as very good compressive strength. This is in particular true for microcapsules with a hydrated cementitious shell thickness in the range of 0.1-10 µm. Such kinds of microcapsules further feature in general a high load capacity which makes them suitable for different kind of release applications. Especially microcapsules of spherical and/or ellipsoidal shape with an average outer diameter in the range of 0.5-500 µm feature an optimal ratio of surface to volume or load capacity in various release applications.

However, the outer diameter of the microcapsule may be smaller than 0.5 µm and/or larger than 500 µm. As well, the thickness of the microcapsule shell can be smaller than 0.1 µm and/or larger than 10 µm.

In particular, the shell of the microcapsule is at least partially made from hydrated spherical or non-spherical particles, platelets or needles with the longest dimension being 10-10000 nm, preferred 50-5000 nm, more preferred 100-1000 nm. According to a preferred embodiment, the shell is solely made from hydrated spherical or non-spherical particles, platelets or needles with the longest dimension being 100-1000 nm. As can be shown, the use of particles in such a size range results in the formation of capsule shells with a unique microstructure that in general improves the overall mechanical stability of the microcapsules.

It is nevertheless possible to make the microcapsules from hydrated cementitious material with particle sizes of less than 100 nm and/or more than 1000 nm. For certain specific applications, this may even be advantageous.

In a highly preferred embodiment, the capsule shell features a porous structure. Preferably, the shell features a mesoporous structure, in particular with a pore size of 2-100 nm. Microcapsules with such porous structures are highly suitable for various release applications in different fields of technology. This is especially true for pore sizes in the range of 2-100 nm that allows for a controlled diffusion of various chemicals and/or reagents in and/or out of the microcapsule. Due to the use of hydrated cementitious material as a component in the capsule shell, the mechanical stability is maintained despite the porosity of the shell.

But in general it is as well possible to provide microcapsules with dense shell structure and/or to provide porous microcapsules with pore sizes below 2 nm and/or above 100 nm. Depending on the application, such kind of microcapsules may even be beneficial.

In an advantageous embodiment, the hollow space (i.e. cavity) within the microcapsule is at least partially filled with a specific gas, a liquid and/or a solid. Preferably, the hollow space is at least partially filled with a salt, a polymer, a drug, a biomolecule, a cell, a living cell, a fragrance, a flavor, enzymes, catalytic materials, flame retarders, phase change materials, absorbers and/or a dye. This allows the microcapsule to be used as a load-carrying member in various release applications.

However, it may as well be beneficial to provide a microcapsule with the hollow space being filled with air or any nonfunctional substance.

The solution of the invention in view of the method for the production of a microcapsule is specified by the features of claim 20. According to the invention, the method comprises the steps of:
a) preparing of a suspension of particulate cementitious material in a solvent,
b) preparing an emulsion or foam by mixing the suspension of step a) with an immiscible fluid or with air, so that:
   (i) the suspension is present as a dispersed phase in the immiscible fluid or air which is acting as a dispersion medium or so that
   (ii) the fluid or air is present as the dispersed phase in the suspension which is acting as the dispersion medium, such that the particulate material of the suspension adsorbs at least partially at the interphase between the immiscible fluid and the suspension,
c) allowing the particulate material adsorbed at the interphase to hydrate with the formation of an individual microcapsule.

In principle, the term "fluid" stands for any free-flowing substance such as e.g. a gas and/or a liquid. A fluid may even be a mixture of different free-flowing substances.

The crucial parameter which determines whether or not the particles adsorb at the phase boundary between the fluid and the suspension is the contact angle θ between the liquid-fluid interface and the particle surface [Finkle, P., H. D. Draper, and J. H. Hildebrand, The theory of emulsification. Journal of the American Chemical Society, 1923. 45(1): p. 2780-2788; Binks, B. P. and S. O. Lumsdon, Influence of particle wettability on the type and stability of surfactant-free emulsions. Langmuir, 2000. 16(23): p. 8622-8631]. With water as solvent and an organic solvent as immiscible fluid, a contact angle θ of around 70° leads e.g. to the formation of stable "oil-in-water emulsion", whereas one of around 110° results in "water-in-oil emulsions" [Kaptay, G., On the equation of the maximum capillary pressure induced by solid particles to stabilize emulsions and foams and on the emulsion stability diagrams. Colloids and Surfaces a-Physicochemical and Engineering Aspects, 2006. 282: p. 387-401].

In general, the dispersed phase can be loaded with one or more of the following substances:
(i) with a catalyst promoting any reaction of the capsule shell material to modify its physical, chemical or microstructural properties and/or
(ii) with any type of material to be encapsulated, namely any type of gas, liquid or solid and any type of chemicals as well as materials like salts, monomers, polymers, drugs, bio molecules, cells, living cells, fragrances, flavors, dyes, enzymes, catalytic materials, flame retarders, phase change materials, absorbers etc., and mixtures of these materials and/or
(iii) with an additional particulate material such as a hydratable inorganic material, metallic, polymeric, ceramic particles and mixtures thereof.

For certain formulations it has been observed that it is advantageous to dilute the emulsion or foam of step b) in order to better obtain single capsules. In some cases the emulsion is too concentrated to obtain single capsules after the cementitious material is hydrated. In such cases dilution of the emulsion prior to the hydration of the material makes sure that the material can hydrate into separated capsules. The dilution factor should be at least 2, more preferably 10 to 20.

According to a first preferred method, the solvent used for preparing the suspension in step a) is a hydrophobic liquid, in particular an organic solvent and/or the fluid used for preparing the dispersion in step b) is an aqueous solvent, in particular water. It is as well possible to use mixtures of different aqueous solvents. The hydrophobic fluid is in particular a fluid that is miscible with water in amounts of up to at most 1% v/v referred to the total volume of the mixture. In particular the hydrophobic fluid is an organic solvent with six or more carbon atoms. Especially, the organic solvent is selected from hexane and/or toluene. As well, the hydrophobic fluid or the organic solvent may be a mixture of different fluids and/or organic solvents, respectively. The aqueous solvent may e.g. be selected from water, short chain alcohols and/or glycols.

However, according to a second preferred method the solvent used for preparing the suspension in step a) is a hydrophilic liquid, in particular water, and/or the fluid used for preparing the dispersion in step b) is a non-aqueous solvent, in particular an organic solvent. Advantageously, the hydrophilic fluid is selected from water, short chain alcohols and/or glycols. The non-aqueous solvent may preferably be an organic solvent, such as hexane and/or toluene. The non-aqueous solvent may be a mixture of different non-aqueous solvents.

In another preferred embodiment, the fluid for preparing the dispersion in step b) is a gas, in particular air. In this case the inventive method comprises producing of a foam which is preferably diluted in order to obtain individual or spaced apart microcapsules.

Preferably, the solvent and/or the particulate cementitious material used in step a) is treated with a surface modifying substance in order to adjust a hydrophobicity of the particulate cementitious material. This allows for a stabilization of the dispersions or emulsions formed during step b). Even though there are various particles which exhibit an optimal intermediate wettability by nature, other materials feature non-ideal wetting properties and are therefore not a priori efficient in stabilizing dispersions or emulsions. Hence, their wetting properties can be tailored by addition of surface modifying substances. This allows for the synthesis of particle-stabilized microcapsules from a wide variety of cementitious materials.

Preferably, the surface modifying substance is an amphiphilic substance, in particular selected from the groups of phosphates, phosphonates, sulfates, sulfonates, alcohols, amines, amides, pyrrolidines, gallates, carboxylic acids and/or corresponding salts. Especially, the surface modifying substance comprises propyl gallate and/or octyl gallate. These substances have been proven to be highly compatible with various cementitious materials.

In principle, other surface modifying substance may be used as well. However, the choice of cementitious materials may be reduced due to compatibility problems.

In case surface modifying molecules are added, the following sequence has shown to be beneficial: First, the surface modifying molecules are added to the solvent. Subsequently, the particulate material is added to the solvent under constant stirring. Preferably, the suspension is then homogenized e.g. on a ball mill for typically 16 hours. This procedure ensures an effective powder desagglomeration and a maximal adsorption of the surface modifying molecules.

In principle it is nevertheless possible to deviate from the above mentioned sequence. This may however require additional measures in order to obtain powder desagglomeration and adsorption of the surface modifying molecules.

Optionally, additional particulate material is added to the suspension in step a), in particular non-hydraulic particulate material, preferably metallic, polymeric and/or ceramic particulate material. However the additional particulate material may as well be another cementitious material.

According to another preferred embodiment, a further suspension of further particulate cementitious material and/or additional particulate material is prepared and mixed with the suspension of step a), whereby preferably the further solvent of the further suspension is miscible with the solvent of the suspension of step a).

The addition of additional particulate material to the suspension of step a) and/or the mixing of at least two suspensions allows for a flexible and efficient tuning of the mechanical and chemical properties of the microcapsules.

Especially, the dispersion of step b) is diluted with a diluting agent in order to obtain a dispersion comprising the dispersed phase as individual spheres and/or bubbles spaced apart from each other within the dispersion medium. In particular, the diluting agent is miscible with the dispersion medium. However, diluting is optional and may be omitted if e.g. the concentration of the dispersion is adequate.

Preferably, a set accelerator is added to the dispersion. The use of a set accelerator is beneficial since it speeds up the hydration (hardening) of the cementitious material. This allows for a better control of the overall production process of the microcapsules. Preferably, the set accelerator is an inorganic salt, especially lithium carbonate ($Li_2CO_3$) and/or sodium carbonate ($Na_2CO_3$). However the use of a set accelerator is not mandatory.

Additionally the particulate material and/or the microcapsule are optionally subjected to surface treatment process in order to implement a specific surface functionality of the microcapsule.

Furthermore, any sort of refinement of the microcapsules may be performed.

Capsules fabricated in the previous steps can as well be transferred to any kind of different solvent and/or any fluids can be removed by a suitable drying method in order to collect dry microcapsules. Such drying is for example helpful if a dissolved substance in the dispersed phase is e.g. to be precipitated at the inside of the capsule shell.

Other advantageous embodiments and combinations of features come out from the detailed description below and the totality of the claims.

BRIEF DESCRIPTION OF THE DRAWINGS

The drawings used to explain the embodiments show:

FIG. 4 Scanning electron micrographs (recorded on a LEO 1530; LEO Elektronenmikroskopie GmbH, Germany) of a:

Figure 5:
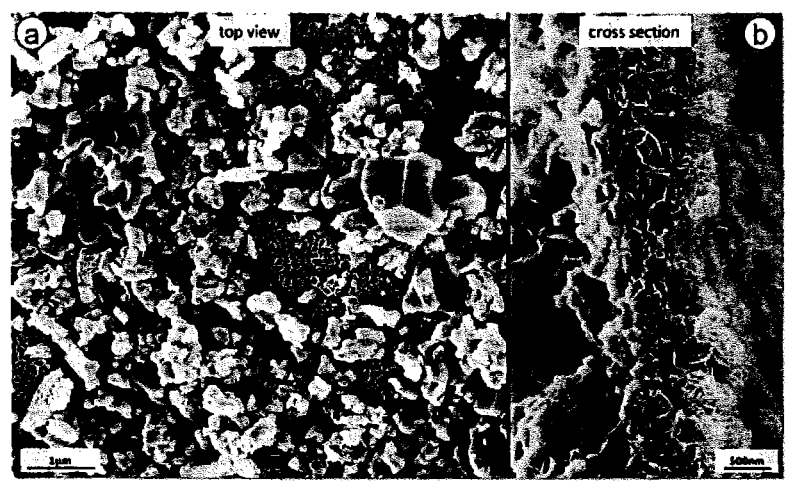
Figure 6:
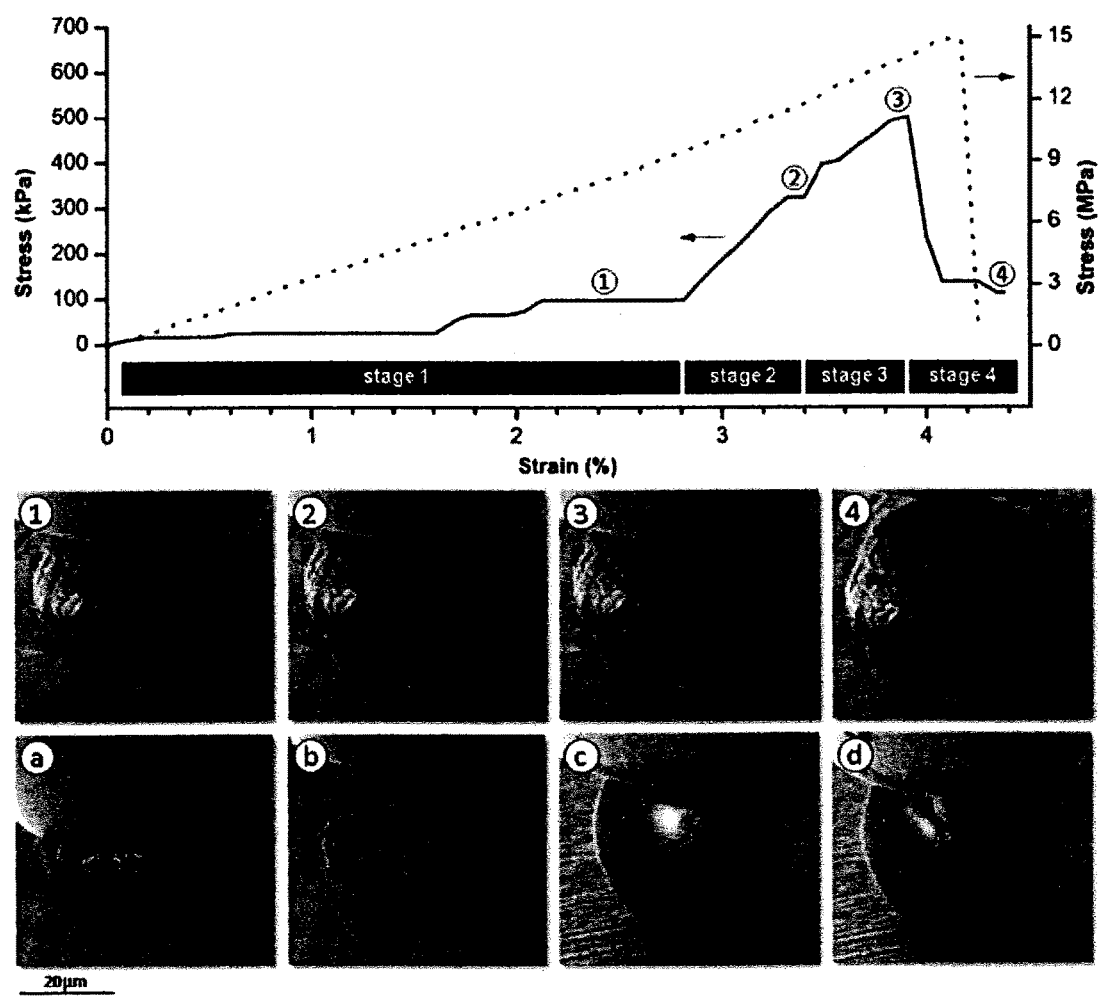

a batch of calcium aluminate microcapsules with a median capsule size $d_{50}$ of 104 µm and b: a close up of a single capsule;

FIG. 5 Scanning electron micrographs (recorded on a LEO 1530; LEO Elektronenmikroskopie GmbH, Germany) of a: the top view on a calcium aluminate microcapsule and b: a cross section of the capsule shell. The capsule inside is on the right hand side of the cross section;

FIG. 6 Stress-strain curve of a mesoporous calcium aluminate microcapsule (solid line) and a dense aluminosilicate capsule (dotted line) recorded from a micro compression test made in a conventional scanning electron microscope (top panel). Electron micrograph snap shots at different states of deformation indicated in the stress-strain curve (medium panels 1-4). The mesoporous calcium aluminate capsule shell deformed to extremely small radii of curvature (bottom panel a) and relaxation of the same shell after deloading (bottom panel b). Brittle fracture behavior of the dense shell of aluminosilicate capsules (bottom panel c, d).

PREFERRED EMBODIMENTS

Example 1

Microcapsule from Hydrated Cementitious Material

Figure 1:
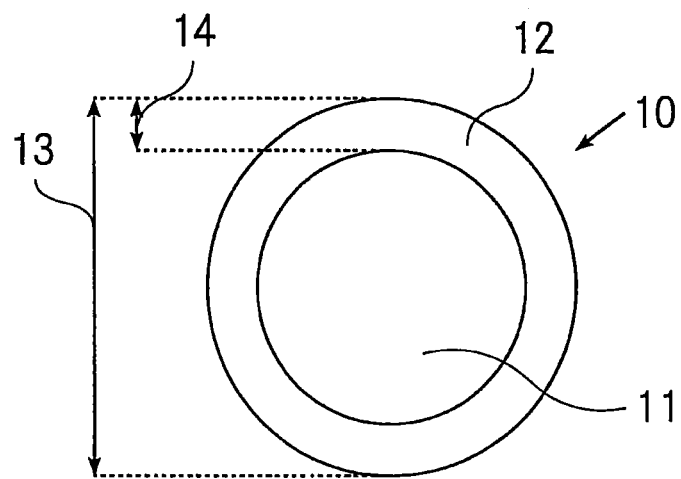
FIG. 1 A schematic representation of a microcapsule in a cross sectional view.

FIG. 1 shows a schematic representation of a first microcapsule 10 in a cross sectional view. The microcapsule 10 is essentially of spherical shape and comprises a hollow capsule core 11 encased by a capsule shell 12. The capsule shell 12 is made of hydrated cementitious material, e.g. hydrated calcium aluminate or another hydrated cementitious material, and features a mesoporous structure with a pore size in the range of approximately 2-100 nm. An outer diameter 13 of the microcapsule 10 is e.g. about 100 µm whereas a thickness 14 of the capsule shell 12 is for example about 1 µm.

Example 2

Microcapsule with Two-layer Structure

Figure 2:
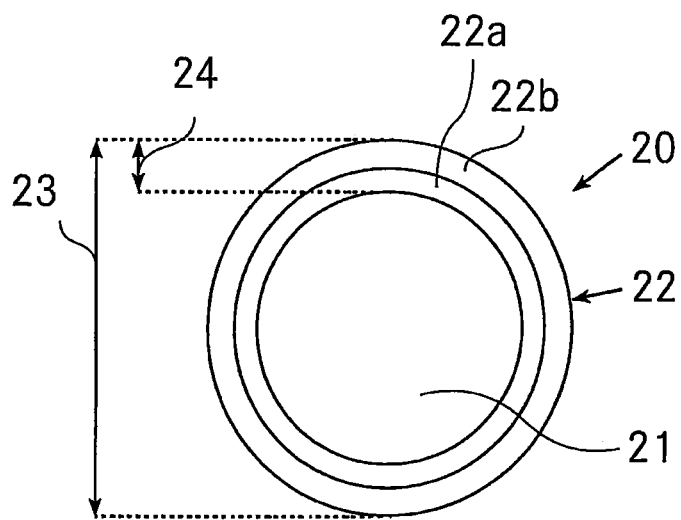
FIG. 2 A schematic representation of cross section through a microcapsule with a two layer capsule shell.

FIG. 2 shows a schematic representation of a second microcapsule 20 in a cross sectional view. As the first microcapsule 10, the second microcapsule consists of a hollow capsule core 21 which is encased by a capsule shell 22. An outer diameter 23 and a thickness 24 the capsule shell 22 of the second microcapsule 20 are for example similar to those of the first microcapsule 10.

In contrast to the first microcapsule 10, the capsule shell 22 of the second microcapsule 20 features a two-layer structure. Hereby, an inner layer 22a is for example made of hydrated cementitious material, e.g. hydrated calcium aluminate, whereas the outer layer 22b is for example made of a non-hydraulic material, e.g. aluminum oxide. Consequently, the outer layer 22b is essentially free of hydrated cementitious material.

Example 3

Water-in-oil Inorganic Microcapsules from Hydrated Cementitious Material

Figure 3:
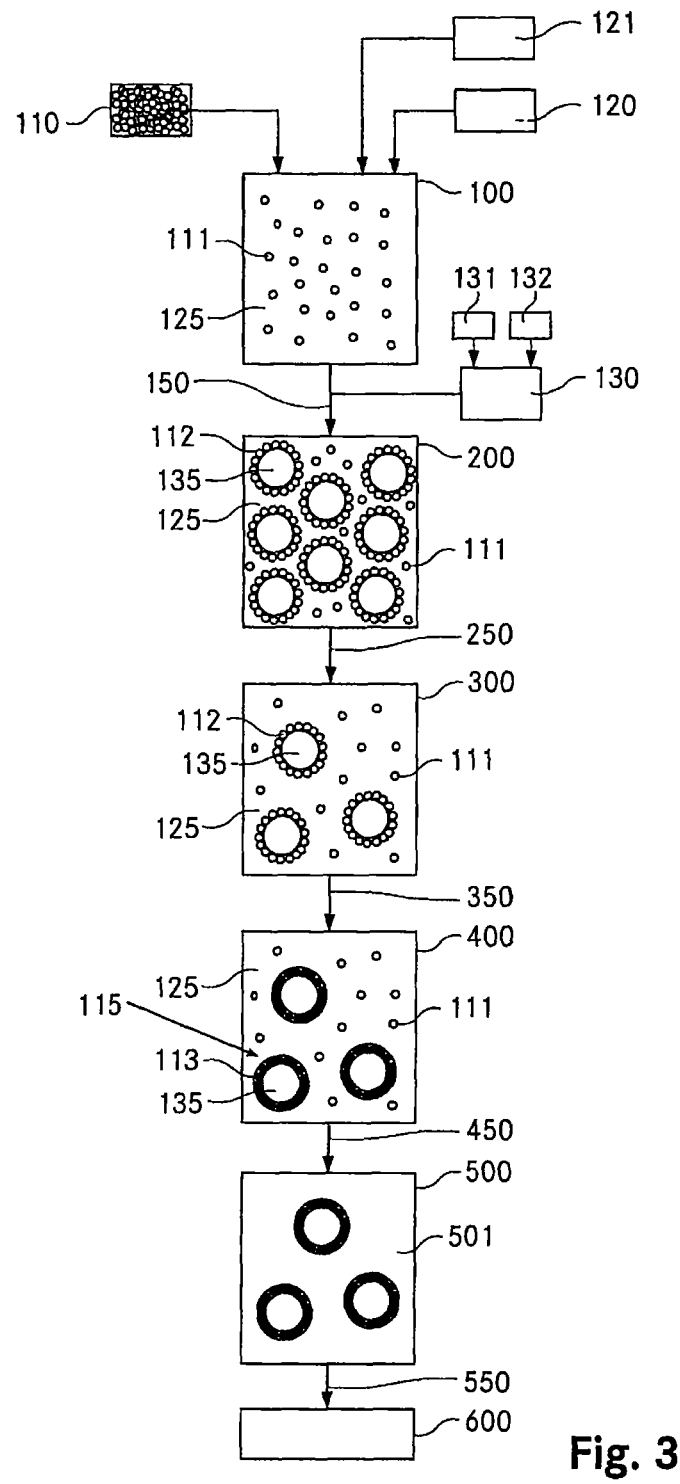
FIG. 3 A schematic representation of a processing route to mesoporous microcapsules from cementitious materials.

FIG. 3 shows a representation of a method for the production of microcapsule from cementitious materials.

In a first step, cementitious particulate material 110, e.g. as-received calcium aluminate powder is dispersed in a solvent 125 at a volume fraction of e.g. 20%. The solvent 125 comprises for example toluene 120 (a non-aqueous solvent) and a surface modifying substance 121, e.g. octyl gallate, in an adequate quantity to disperse the initially hydrophilic particulate material 110 in toluene without losing their ability to adsorb to the liquid-liquid interface. Specifically, calcium aluminate powder (Type: CA-14W, density 3.11 gcm$^{-3}$, $d_{10}$: 1.7 µm, $d_{50}$: 14.0 µm, $d_{90}$: 57.6 µm, Almatis, Germany) is dispersed in toluene (purisse, Fluka, Switzerland) containing a quantity of 2.9 µmolm$^{-3}$ octyl gallate (Sigma-Aldrich, Switzerland) to adjust the particle wetting properties.

The so formed suspension 100 is then ball milled for 16 h, e.g. in 250 ml HD-PE bottles using alumina milling balls of 1 cm diameter. Thereby the powder agglomerates are destroyed and the particle surface is hydrophobized through adsorption of octyl gallate. This results in hydrophobized cementitious particles 111 being homogeneously suspended in the solvent 125 or the toluene, respectively.

Subsequently, a fluid in the form of an aqueous solution 130 of a set accelerator 131, for example 10 gL$^{-1}$ Li$_2$CO$_3$ set accelerator in water 132, is prepared. The set accelerator 131 is added in order to ensure a rate controlled hydration reaction and to compensate for the hydration retardation caused by the octyl gallate 121.

In a subsequent emulsifying step 150, the aqueous solution 130 is then vigorously mixed with the cement suspension 100 in a volume ratio of 2:3 yielding a concentrated water-in-oil emulsion 200. Specifically, the emulsion 200 is made by mixing the suspension 100 with 40 vol % of ultrapure water (18.2 MΩ, Barnstead NANOpure Diamond, Thermo Fisher Scientific Inc, USA) containing 10 gL$^{-1}$ of Li$_2$CO$_3$ (purum, Fluka, Switzerland) as a set accelerator 131 for calcium aluminate cement. Mixing is done using a kitchen mixer at full speed for 90 s (Braun Multiquick, Braun GmbH, Germany).

Due to the high adsorption energy of the modified cement particles at the water-oil-interface, cement particles 111 start to adsorb at the surface of the water droplets 135 or the liquid-liquid interface, respectively. Upon 20 times dilution of the concentrated emulsion 200 in a dilution step 250, e.g. with toluene, individual and spaced apart water droplets 135 decorated with adsorbed cement particles 112 in a diluted emulsion 300 can be observed.

Since the cement particles 112 at the surface of the water droplets 135 are now in contact with the water, a hydration reaction of the cementitious particles 112 starts at the surface of the water droplets 135 and proceeds to the outside. During this hydration step 350, a dispersion 400 with individual microcapsules 115 consisting of partially or fully hydrated particles 113 are formed.

After a specific time (e.g. 1 hour) after the start of the hydration reactions at temperatures between 0° C. and 60° C., the toluene phase is removed subsequent to sedimentation of the capsules in a subsequent purifying step 450. Thereby, to stop any additional hydration reaction, the toluene supernatant is removed and the capsules are washed 3 times with a suitable liquid 501, e.g. ethanol. This results in a purified dispersion 500 of individual microcapsules 115 being suspended in the liquid 501.

In a final drying step 550, the microcapsules are separated from the liquid 501 and any residual particles 111 by filtration and harvested as a dry powder 600.

Figure 4:
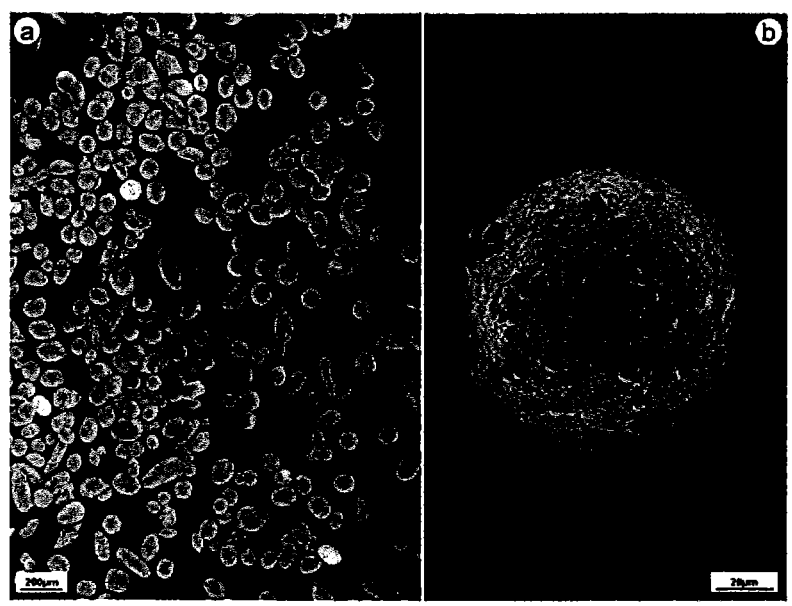

About eight million hollow and dry calcium aluminate microcapsules can be collected per batch of 33 ml aqueous and 39 ml organic solvent plus 31 g of powder (FIG. 4a) corresponding to a yield of 65 wt % capsules based on the cement powder input. This yield could be further increased by lowering the calcium aluminate powder fraction in the suspension. The capsules are spherical to elongated in shape. Their size distribution is characterized by a $d_{50}$ of 104 µm as well as 61 µm and 149 µm for $d_{10}$ and $d_{90}$, respectively. Typically more than 85% are free of defects when using this laboratory approach. The mean capsule size can be tailored between −30 and −200 µm by varying the shear rate during emulsification.

The capsule's surface is shown in FIG. 4b. Due to the broad particle size distribution of the as-received powder, this surface is rather rough. This roughness might be of advantage if such capsules are incorporated into a polymeric matrix. In this case, the polymer adhesion to the capsule wall is expected to be very strong due to physical interlocking.

Zooming in on the capsule surface reveals a continuous layer of percolating calcium aluminate hydrate crystals (FIG. 5a). According to Lee et al. "Castable refractory concretes", International Materials Reviews, 2001. 46(3): p. 145-167, the predominant hydrate phase is 2 CaO.Al$_2$O$_3$.8 H$_2$O as a result of cement hydration at room temperature. The shell is around 500 nm in thickness and features a mesoporous microstructure formed through the cement hydration at the water-oil interface (FIG. 5b). The pore diameters are below 100 nm and it seems that pores are only moderately interconnected. It is important to note that a single pore is trapped in the percolating crystal network and does not connect through the entire capsule shell which justifies using the term mesoporous. Variations in shell thickness are attributed to the broad particle size distribution of the calcium aluminate powder. It is clearly visible that the cement hydration reaction starts from the inside of the capsule (from the right hand side of the cross section) and progresses to the outer side, where residual, poorly reacted primary particles still can be observed.

Micromechanical compression tests in a conventional scanning electron microscope (SEM) are carried out to characterize the mechanical behavior of the entire capsule structure. Specifically, micromechanical tests are conducted in a conventional scanning electron microscope (Zeiss DSM 962) with a piezo driven compression test setup. Capsules are compressed on a SEM sample holder installed on a 50 g load cell of 2 mg resolution with a truncated diamond tip of 50 μm radius (SYNTON-MDP, Switzerland). For testing, the tip is driven at 10 μm in 60 s, load and displacement data are sampled at a frequency of 5 Hz. In addition, an SEM video is taken at a frame rate of 1 Hz. To reduce charging effects, the tip is gold coated before use.

To link mechanical with microstructural properties, commercially available, dense aluminosilicate cenospheres of comparable size and wall thickness are measured in addition to our mesoporous calcium aluminate microcapsules. During testing, the deformation behavior of the capsules is recorded sampling load displacement data and taking SEM videos at 1 Hz. The nominal compressive stress that a single capsule is able to bare is calculated by dividing compressive load by the projective area of the unloaded capsule. Ten nearly-spherical microcapsules are tested for each capsule type for statistics. Typical stress-strain curves of mesoporous calcium aluminate microcapsules (solid line) and dense aluminosilicate cenospheres (dotted line) are plotted in FIG. 6, top panel. The stress-strain curves of the cementitious microcapsules show typically four stages. In stage 1, minor rearrangements are monitored at low compressive loads. These rearrangements are induced by deviations from a perfectly round shape and the shell roughness. During stage 2, the capsule is subject to true compression and a linear evolution of the strain curve is observed with increasing stress. Initiation of a macro crack occurs at 323 kPa where the plateau appears in the stress-strain curve. However, this crack does not propagate catastrophically through the entire capsule wall as the electron micrograph snap shots prove (FIG. 6, middle panel). Instead, the capsule can be loaded with additional 177 kPa until the shell reaches the point of mechanical breakdown (end of stage 3). Stage 3 of the compression test is therefore governed by subcritical crack growth within the capsule cement wall. Interestingly, the crack closes again after deloading in stage 4, indicating a significant elastic energy in the capsule shell. This crack tolerant behavior observed for all the tested calcium aluminate microcapsules is attributed to their highly porous shell. The damage introduced by a propagating crack is locally confined by the dimension of a cement crystal. Breaking of a crystal leads to a temporary relaxation and load has to be transferred to and concentrated at neighboring crystals before further local damage appears. During this process, a propagating crack is deflected multiple times dissipating elastic energy. This fracture mode of our mesoporous capsules allows them to be bent to extremely small radii of curvature (FIG. 6, bottom panel a). In addition, the relaxation after deloading of the same shell demonstrates the elastic behavior of the porous capsule that is unexpected for inorganic materials (FIG. 6, bottom panel b). By contrast, the dense shell microstructure of aluminosilicate cenospheres exhibits a very brittle fracture mode, as expressed by the dashed stress-strain curve in FIG. 4. Upon loading, no rearrangements and a linear evolution of the curve from the beginning on are observed. As expected, the densely walled aluminosilicate cenosphere is found to bare a much higher stress (15 MPa) compared with cement capsules with porous walls (0.5 MPa). But once the peak load is exceeded, the dens capsules break in two or more fragments under catastrophic crack propagation. In fact, crack propagation is too fast to be followed at a frame rate of 1 Hz.

A summary of the microstructural and mechanical properties of porous calcium aluminate microcapsules and dense aluminosilicate cenospheres is given in Table 1. Both, microcapsules and cenospheres, have comparable shell thicknesses allowing for a comparison of their mechanical properties. The calcium aluminate capsules as well as the aluminosilicate cenospheres show a linear elastic behavior with strains which are surprisingly high for purely inorganic materials. This elasticity is attributed to the small dimensions of the capsule walls. The scattering of the data is substantial for both capsule samples and a consequence of the non-uniform shell thicknesses. Due to the dense microstructure of the cenospheres, their compressive strength is 73 times higher compared with the one measured for mesoporous capsules. The most striking difference between the two types of capsules, however, is the tough fracture mode of the mesoporous calcium aluminate capsules which contrasts to the brittle one of the dense aluminosilicate capsules.

TABLE 1

Overview of capsule microstructures and corresponding mechanical properties averaged over 10 measurements.

|  | Calcium aluminate microcapsules | Aluminosilicate cenospheres |
|---|---|---|
| Average capsule diameter (pm) | 32 | 38 |
| Range of shell thicknesses (nm) | 400-1,000 | 400-900 |
| Shell microstructure | mesoporous | dense |
| Compressive strength (MPa) | 0.27 ± 0.12 | 27.00 ± 11.58 |
| Strain at break (%) | 3.03 ± 1.47 | 4.41 ± 1.22 |
| Mechanical behavior | elastic | elastic |
| Failure mode | tough | brittle |

With a novel processing route based on non-aqueous solvents that combines emulsion templating and in-situ particle hydrophobization, large numbers of microcapsules can be fabricated. Emulsion templating guarantees for an efficient loading of the capsules and the in-situ particle hydrophobization technology potentially enables the use of a broad variety of materials. We synthesized capsules from calcium aluminate cement, one example for a material that hydrates at the water-oil interface leading to the formation of mesoporous capsule shells. Owing to their unique microstructure, calcium aluminate microcapsules show very interesting mechanical properties, namely an excellent crack tolerance and elasticity, coupled with good compressive strength. In addition, it will be possible to fine tune the mesoporous shell by deliberately controlling the reaction temperature and by using suitable additives which makes these capsules interesting for release applications. Last but not least, calcium aluminate is stable also at high temperatures, chemically inert and harmless to the environment.

Example 4

Water-in-oil Inorganic Microcapsules from Ground Blast Furnace Slag

An organic suspension was prepared adding 25 vol % of ground blast furnace slag (GBFS) (Holcim, Spinor A6) to hexane together with 0.901 wt % (to powder) octyl gallate surface modifier. This suspension was homogenized for 16 h on a ball mill. Thereafter, the suspension was diluted to 10 vol % solids loading with additional hexane. The diluted suspension was then emulsified with an aqueous phase consisting of a solution of 100 gL$^{-1}$ sodium carbonate set accelerator in water. The total emulsion volume consisted of 60 vol % diluted suspension and 40 vol % aqueous phase. The freshly produced water-in-oil emulsion was subsequently diluted 21 times with hexane resulting in a dispersion of GBFS wet microcapsules. A hydration time of 1 d at room temperature yielded mechanically stable microcapsules that allowed for a solvent transfer or for complete removal of the solvents.

Example 5

Oil-in-water Inorganic Microcapsules from Ground Blast Furnace Slag

An organic suspension was prepared adding 25 vol % of ground blast furnace slag (GBFS) (Holcim, Spinor A6) to hexane together with 0.541 wt % (to powder) octyl gallate surface modifier. This suspension was homogenized for 16 h on a ball mill. Thereafter, the suspension was diluted to 10 vol % solids loading with additional hexane. The diluted suspension was then emulsified with an aqueous phase consisting of a 40° C. warm solution of 500 gL$^{-1}$ sodium carbonate set accelerator in water. The total emulsion volume consisted of 60 vol % diluted suspension and 40 vol % aqueous phase. The freshly produced oil-in-water emulsion was subsequently diluted 21 times with water resulting in a dispersion of GBFS wet microcapsules. After hydration at room temperature mechanically stable microcapsules were produced that allowed for a solvent transfer or for complete removal of the solvents.

Example 6

Water-in-oil Inorganic Microcapsules from Calcium Aluminate Cement

An organic suspension was prepared adding 20 vol % of calcium aluminate (CA) powder (Almatis, CA-14W) to toluene together with 0.291 wt % (to powder) octyl gallate surface modifier. This suspension was homogenized for 16 h on a ball mill. The homogenized suspension was subsequently emulsified with an aqueous dispersed phase consisting of a solution of 10 gL$^{-1}$ lithium carbonate set accelerator in water. The total emulsion volume consisted of 60 vol % diluted suspension and 40 vol % aqueous phase. The freshly produced water-in-oil emulsion was then diluted 21 times with toluene resulting in a dispersion of CA wet microcapsules. A hydration time for 1 h at room temperature yielded mechanically stable microcapsules that allowed for a solvent transfer or for complete removal of the solvents.

Example 7

Water-in-oil Cement/Alumina Composite Capsules With the Alumina at the Inside of the Capsule Wall An organic suspension (S1) was prepared mixing 25 vol % ground blast furnace slag (GBFS) (Holcim, Spinor A6) and 0.567 wt % (to powder) octyl gallate in toluene. In addition, another organic suspension (S2) was prepared adding 20 vol % of alumina powder (Almatis CL2500SG) to toluene together with 0.034 wt % (to powder) octyl gallate surface modifier. Suspensions S1 and S2 were both homogenized for 16 h on a ball mill. Then both suspensions were diluted to 15 vol % solids loading with additional toluene and a mix with 30% diluted S1 70% diluted S2 was prepared. This mix was then emulsified with an aqueous dispersed phase consisting of a 40° C. warm solution of 500 gL$^{-1}$ sodium carbonate set accelerator in water. The total emulsion volume consisted of 60 vol % suspension mix and 40 vol % aqueous phase. The freshly produced water-in-oil emulsion was then diluted 21 times with toluene resulting in a dispersion of GBFS/alumina wet microcapsules. After hydration at 40° C. for 3 h mechanically stable microcapsules were produced that allowed for a solvent transfer or for complete removal of the solvents. The shell of these capsules is made of a layered composite with the outer layer consisting of partially hydrated GBFS and the inner layer consisting of alumina particles. The GBFS acts thereby as binder for the alumina layer.

Example 8

Water-in-oil Cement/Alumina Composite Capsules with the Alumina at the Outside of the Capsule Wall An organic suspension (S1) was prepared mixing 25 vol % ground blast furnace slag (GBFS) (Holcim, Spinor A6) and 0.567 wt % octyl gallate in toluene. In addition, another organic suspension (S2) was prepared adding 20 vol % of alumina powder (Almatis CL2500SG) to toluene together with 0.161 wt % (to powder) octyl gallate surface modifier. Suspensions S1 and S2 were both homogenized for 16 h on a ball mill. Then both suspensions were diluted to 15 vol % solids loading with additional toluene and a mix with 30% diluted S1 70% diluted S2 was prepared. This mix was then emulsified with an aqueous dispersed phase consisting of a 40° C. warm solution of 500 gL$^{-1}$ sodium carbonate set accelerator in water. The total emulsion volume consisted of 60 vol % suspension mix and 40 vol % aqueous phase. The freshly produced water-in-oil emulsion was then diluted 21 times with toluene resulting in a dispersion of GBFS/alumina wet microcapsules. After hydration at 40° C. for 3 h stable microcapsules were produced that allowed for a solvent transfer or for complete removal of the solvents. The shell of these capsules is made of a layered composite with the outer layer consisting of alumina particles and the inner layer consisting of hydrated GBFS particles. The GBFS acts thereby as binder for the alumina layer.

Example 9

Encapsulation of Particles into Inorganic Water-in-oil Microcapsules

An organic suspension (S1) was prepared mixing 25 vol % ground blast furnace slag (GBFS) (Holcim, Spinor A6) and 0.567 wt % octyl gallate (to powder) in toluene. Suspension S1 was then homogenized for 16 h on a ball mill. Subsequently, S1 was diluted to 15 vol % solids loading with additional toluene. An aqueous suspension (S2) was prepared adding 10 vol % of GBFS (Holcim, Spinor A6) together with 500 gL$^{-1}$ sodium carbonate set accelerator into 40° C. warm water. Suspension S1 and suspension S2 were then emulsified to form a water-in-oil emulsion. The total emulsion volume consisted of 60 vol % organic suspension S1 and 40 vol % aqueous suspension S2. This emulsion was then diluted 21 times with toluene resulting in a dispersion of GBFS wet microcapsules with GBFS particles enclosed within the capsule core. After hydration at 40° C. for 2 h mechanically stable microcapsules were produced that allowed for a solvent transfer or for complete removal of the solvents.

Example 10

Encapsulation of a Polymer into Inorganic Water-in-oil Microcapsules

An organic suspension (S1) was prepared mixing 25 vol % ground blast furnace slag (GBFS) (Holcim, Spinor A6) and 0.709 wt % octyl gallate (to powder) in hexane. It was then homogenized for 16 h on a ball mill. Subsequently, the suspension was diluted to 15 vol % solids loading with additional hexane. A 40° C. warm, aqueous solution of 1 vol % poly(ethyleneimine) (PEI) (600,000-1,000,000, 50 wt % aqueous solution, Fluka) and 500 $gL^{-1}$ sodium carbonate set accelerator was made. The organic suspension S1 and the aqueous solution were then emulsified to form a water-in-oil emulsion. The total emulsion volume consisted of 60 vol % organic suspension S1 and 40 vol % aqueous solution. This emulsion was then diluted 21 times with hexane resulting in a dispersion of GBFS wet microcapsules with PEI enclosed within the capsule core. After hydration at 40° C. for 2 h stable microcapsules were produced that allowed for a solvent transfer or for complete removal of the solvents.

Example 11

Encapsulation of a Water Soluble Substance Into Inorganic Microcapsules

An organic suspension was prepared adding 25 vol % of ground blast furnace slag (GBFS) (Holcim, Spinor A6) to hexane together with 0.709 wt % (to powder) octyl gallate surface modifier. This suspension was homogenized for 16 h on a ball mill. Thereafter, the suspension was diluted to 15 vol % solids loading with additional hexane. The diluted suspension was then emulsified with a 40° C. warm aqueous phase containing 500 $gL^{-1}$ sodium carbonate as the encapsulated substance. The total emulsion volume consisted of 60 vol % diluted suspension and 40 vol % aqueous phase. The freshly produced water-in-oil emulsion was subsequently diluted 21 times with hexane resulting in a dispersion of GBFS wet microcapsules. A hydration time of 3 h at 40° C. yielded mechanically stable microcapsules. Upon drying of the capsules, the sodium carbonate precipitates at the inside of the inorganic capsule wall.

Example 12

Air-in-water Inorganic Microcapsules from Calcium Aluminate Cement

An aqueous solution was prepared by adding 2wt % propyl gallate (to cement powder) to water displaying a pH higher than 10. 48.3 vol % of calcium aluminate cement (Almatis, CA-270) and 3.4 vol % lithium carbonate ($Li_2CO_3$, Fluka) were dry mixed and subsequently stirred in to the aqueous solution. This suspension was directly foamed without a ball milling step. The freshly produced foam was then diluted 21 times with water resulting in a dispersion of calcium aluminate cement microcapsules. A hydration time of 1 d at room temperature yielded mechanically stable microcapsules that allowed for a solvent transfer or for complete removal of the solvents.

Example 13

Air-in-water Calcium Aluminate/Alumina Composite Microcapsules

An aqueous suspension was prepared by adding 50 vol % of alumina powder (Ceralox, HPA-0.5) to an aqueous solution displaying a pH higher than 10 and containing 0.18 wt % propyl gallate. This suspension was homogenized for 16 h on a ball mill. The homogenized suspension was then diluted to 22.4 vol % alumina powder, the propyl gallate concentration was raised to 2 wt % and the pH was set to 9.9. A dry-mixture containing 22.5 vol % calcium aluminate cement and 1.1 vol % lithium carbonate was stirred into the suspension. The suspension was foamed and the freshly produced foam was then diluted 21 times with water resulting in a dispersion of calcium aluminate/alumina composite wet microcapsules. A hydration time for 1 d at room temperature yielded mechanically stable microcapsules that allowed for a solvent transfer or for complete removal of the solvents.

Example 14

Oil-in-water Inorganic Microcapsules From Calcium Aluminate Cement

An aqueous solution was prepared by adding 2wt % propyl gallate (to cement powder) to water displaying a pH higher than 10. 48.3 vol % of calcium aluminate cement (Almatis, CA-270) and 3.4 vol% lithium carbonate (Li2CO3, Fluka) were dry mixed and subsequently stirred in to the aqueous solution. Without a ball milling step this suspension was directly emulsified with the total emulsion volume consisting of 60 vol % suspension and 40 vol % octane. The freshly produced emulsion was then diluted 21 times with water resulting in a dispersion of calcium aluminate cement microcapsules. A hydration time of 1 d at room temperature yielded mechanically stable microcapsules that allowed for a solvent transfer or for complete removal of the solvents.

Example 15

Oil-in-water Calcium Aluminate/Alumina Composite Microcapsules

An aqueous suspension was prepared by adding 50 vol % of alumina powder (Ceralox, HPA-0.5) to an aqueous solution displaying a pH higher than 10 and containing 0.18 wt % propyl gallate. This suspension was homogenized for 16 h on a ball mill. The homogenized suspension was then diluted to 22.4 vol % alumina powder, the propyl gallate concentration was raised to 2 wt % and the pH was set to 9.9. A dry-mixture containing 22.5 vol % calcium aluminate cement and 1.1 vol % lithium carbonate was stirred into the suspension. The suspension was emulsified with the total emulsion volume consisting of 60 vol % suspension and 40 vol % octane. The freshly produced emulsion was then diluted 21 times with water resulting in a dispersion of calcium aluminate/alumina composite wet microcapsules. A hydration time for 1 d at room temperature yielded mechanically stable microcapsules that allowed for a solvent transfer or for complete removal of the solvents.

The invention is not restricted on the embodiments discussed above.

In particular, the first microcapsule 10 shown in FIG. 1 and/or the second microcapsule 20 shown in FIG. 20 may be of any suitable shape, in particular of elongated, ellipsoidal or oblate ellipsoidal shape. As well these two microcapsules may exhibit different diameters and/or thicknesses of the capsule shells.

Optionally, the capsule cores 11, 21 of the two microcapsules 10, 20 can be filled, e.g. with a salt, a polymer, a drug, a biomolecule, a cell, a living cell, a fragrance, a flavor and/or a dye.

The second microcapsule 20 shown in FIG. 2 can as well feature a two-layer-structure with the inner layer 22a made of non-hydraulic material, e.g. aluminum oxide, and the outer layer 22b made of hydrated cementitious material, e.g. hydrated calcium aluminate.

Moreover, the second microcapsule may have a multi-layer structure, e.g. with 3, 4, 5, 6, or even more individual layer. Each of these individual layers may consist of hydrated cementitious materials and/or non-hydraulic materials.

As well, the method presented in FIG. 3 may be adapted if required. Thereby, one or more of the method steps can be omitted and/or replaced by other steps. Various adaptions of the method presented in FIG. 3 follow from the above mentioned examples 4-15.

It is for example possible to use another solvent 125 and/or a mixture of different solvents instead of toluene. As well, the surface modifying substance 121 may be omitted and/or another substance than octyl gallate may be used. Additionally, $Li_2CO_3$ as set accelerator 131 can in principal be omitted and/or replaced by another accelerator. Instead of the water-in-oil emulsion 200, an oil-in-water emulsion may be obtained in the emulsifying step 150. The kind of emulsion during the emulsifying step 150 will in particular depend on the agents, substances and conditions chosen in the preceding steps.

Instead of toluene, another liquid may be used in order to dilute the emulsion 200 in the dilution step 250. Preferably, said other liquid is miscible with the solvent 125 or toluene. However, it is in principal possible to completely omit the dilution step 250.

As well the purifying step 450 is optional and may be omitted if the purity of the microcapsule obtainable in the hydration step 350 is satisfactory.

Moreover, the final drying step 550 may be omitted if the microcapsules are e.g. to be used in a liquid.

As well, the aqueous solution 130 used for the emulsifying step 150 may additionally be loaded with a salt, a polymer, a drug, a biomolecule, a cell, a living cell, a fragrance, a flavor and/or a dye. This allows for the encapsulation of said substances within the individual microcapsules 115.

In summary, it is to be noted that a new kind of microcapsules comprising hydrated cementitious material is provided. The inventive microcapsules can be harvested at high yield. They show very interesting mechanical properties, namely an excellent crack tolerance and elasticity, coupled with good compressive strength. Additionally, a new and versatile method allows for a flexible and economic production of microcapsules, in particular microcapsules comprising hydrated cementitious material.

| List of reference signs | |
|---|---|
| 10 | First microcapsule |
| 11 | Hollow capsule core |
| 12 | Capsule shell |
| 13 | Outer diameter of the microcapsule 10 |
| 14 | Thickness of the capsule shell 12 |
| 20 | Second microcapsule |
| 21 | Hollow capsule core |
| 22 | Capsule shell |
| 22a | Inner layer of capsule shell 22 |
| 22b | Outer layer of capsule shell 22 |
| 23 | Outer diameter of the microcapsule 20 |
| 24 | Thickness of the capsule shell 22 |
| 100 | Suspension |
| 110 | Particulate cementitious material (powder) |
| 111 | Suspended particulate cementitious material |
| 112 | Adsorbed particulate cementitious material |
| 113 | Hydrated particles |
| 115 | Individual microcapsule |
| 120 | Non-aqueous solvent, toluene |
| 121 | Surface modifying substance, octyl gallate |
| 125 | Solvent of suspension 100 |
| 130 | Fluid, aqueous solution |
| 131 | Set accelerator |
| 132 | Solvent for set accelerator |
| 135 | Water droplet |
| 150 | Emulsifying step |
| 200 | Concentrated emulsion |
| 250 | Dilution step |
| 300 | Diluted emulsion |
| 350 | Hydration step |
| 400 | Hydrated dispersion |
| 450 | Purifying step |
| 500 | Purified dispersion |
| 501 | Liquid, ethanol |
| 550 | Drying step |
| 600 | Dry powder of microcapsules |

The invention claimed is:

1. A method for the production of a plurality of microcapsules having a hollow capsule space, the method comprising the steps of:
   a) preparing of a suspension of particulate cementitious material in a solvent,
   b) preparing an emulsion or foam by mixing the suspension of step a) with an immiscible fluid, wherein:
      (i) the suspension is present as a dispersed phase in the immiscible fluid as a dispersion medium or
      (ii) the immiscible fluid is present as the dispersed phase in the suspension as the dispersion medium,
   whereby the particulate cementitious material of the suspension adsorbs at least partially at a phase boundary between the immiscible fluid and the suspension, and
   c) allowing the particulate cementitious material adsorbed at the interphase to hydrate with the formation of the microcapsules.

2. The method according to claim 1, wherein the method further comprises, after preparing the emulsion in (b), conducting a dilution step.

3. The method according to claim 1, wherein the solvent comprises a non-aqueous solvent and/or the immiscible fluid is a hydrophilic liquid.

4. The method according to claim 1, wherein the solvent is an aqueous solvent, and/or the immiscible fluid is a hydrophobic liquid.

5. The method according to claim 1, wherein the immiscible fluid is a gas.

6. The method according to claim 1, wherein the method further comprises treating the solvent and/or the particulate cementitious material with a surface modifying substance in order to adjust a hydrophobicity of the particulate cementitious material.

7. The method according to claim 6, wherein the surface modifying substance comprises an amphiphilic substance selected from the groups of phosphates, phosphonates, sulfates, sulfonates, alcohols, amines, amides, pyrrolidines, gallates, carboxylic acids and/or corresponding salts.

8. The method according to claim 1, wherein in step (a) includes adding non-hydraulic particulate material as additional particulate material to the suspension.

9. The method according claim 1, wherein said method further comprises preparing a further suspension in a further solvent of further particulate cementitious material and/or of additional particulate material and mixing it with the suspension of step a), whereby, optionally the further solvent of the further suspension is miscible with the solvent of the suspension of step a).

10. The method according to claim 1, wherein said method further comprises diluting the emulsion of step b) with a diluting agent in order to obtain a dispersion comprising the dispersed phase as individual spheres and/or bubbles spaced apart from each other within the dispersion medium.

11. The method according to claim 10, wherein the diluting agent is miscible with the dispersion medium.

12. The method according to claim 1, wherein said method further comprises subjecting the particulate cementitious material and/or the microcapsules to a surface treatment process in order to implement a specific surface functionality of the microcapsules.

13. The method according to claim 7, wherein the surface modifying substance comprises octyl gallate.

14. The method according to claim 8, wherein the non-hydraulic particulate material comprises metallic, polymeric and/or ceramic material.

15. The method according to claim 9, wherein the additional particulate material comprises metallic particulate material, polymeric particulate material, and/or ceramic particulate material.

* * * * *